US009205158B1

(12) United States Patent
Jacob et al.

(10) Patent No.: US 9,205,158 B1
(45) Date of Patent: Dec. 8, 2015

(54) RETORT WITH BAFFLED SPRAY SYSTEM AND RELATED METHODS

(71) Applicants: Gregory Jacob, Mandeville, LA (US); Beau R. Moreau, Lacombe, LA (US); Philip M. LeBlanc, Franklinton, LA (US)

(72) Inventors: Gregory Jacob, Mandeville, LA (US); Beau R. Moreau, Lacombe, LA (US); Philip M. LeBlanc, Franklinton, LA (US)

(73) Assignee: AllPax Products LLC, Covington, LA (US)

( * ) Notice: Subject to any disclaimer, the term of this patent is extended or adjusted under 35 U.S.C. 154(b) by 0 days.

(21) Appl. No.: 14/282,220

(22) Filed: May 20, 2014

Related U.S. Application Data

(60) Provisional application No. 61/826,836, filed on May 23, 2013.

(51) Int. Cl.

| A61L 9/00 | (2006.01) |
|---|---|
| A61L 2/00 | (2006.01) |
| B08B 9/00 | (2006.01) |
| B08B 9/093 | (2006.01) |
| A61L 2/04 | (2006.01) |
| A61L 2/07 | (2006.01) |

(52) U.S. Cl.
CPC .... *A61L 2/04* (2013.01); *A61L 2/07* (2013.01)

(58) Field of Classification Search
CPC .............. A61L 2/00; A61L 2/07; A61L 2/04; A61L 2/0088

USPC .......... 422/26, 28, 292, 295, 298; 134/22.15, 134/22.18

See application file for complete search history.

(56) References Cited

U.S. PATENT DOCUMENTS

| 2,282,187 | A | 5/1942 | Herold et al. |
|---|---|---|---|
| 3,589,611 | A | 6/1971 | Jones, Jr. |
| 4,060,914 | A | 12/1977 | Hoffman |
| 4,221,638 | A | 9/1980 | Jones, Jr. |
| 4,371,335 | A | 2/1983 | Jones |
| 4,401,051 | A | 8/1983 | Gunther |
| 4,669,667 | A | 6/1987 | Perkins et al. |
| 4,738,617 | A | 4/1988 | Zimmerman |
| 5,561,027 | A | 10/1996 | Verlinden et al. |
| 5,664,482 | A | 9/1997 | Graham et al. |
| 5,685,326 | A | 11/1997 | Cord et al. |
| 6,177,048 | B1 | 1/2001 | Lagerstedt |
| 6,626,087 | B2 | 9/2003 | Roumagnac |
| 7,104,465 | B2 | 9/2006 | Persoons et al. |
| 7,380,978 | B2 | 6/2008 | Damhuis |
| 7,481,972 | B2 | 1/2009 | Christensen et al. |
| 8,277,754 | B2 | 10/2012 | Roumagnac et al. |
| 2005/0013908 | A1 | 1/2005 | Persoons |
| 2005/0198923 | A1 | 9/2005 | Wolters et al. |
| 2011/0111149 | A1 | 5/2011 | Wolters et al. |

FOREIGN PATENT DOCUMENTS

| BE | EP 1 862 082 A2 * | 12/2007 | ............... A23L 3/10 |
|---|---|---|---|
| EP | 1382353 | 7/2003 | |
| EP | 1820410 | 11/2006 | |
| EP | 1862082 | 11/2006 | |
| WO | WO 2006/108812 | 10/2006 | |

* cited by examiner

*Primary Examiner* — Monzer R Chorbaji
(74) *Attorney, Agent, or Firm* — Thompson Hine LLP

(57) ABSTRACT

A retort system for heating product to a specified temperature for sterilization is provided. The system includes a vessel having an associated liquid spraying system where one or more baffles are provided to disrupt sprays from nozzles.

24 Claims, 8 Drawing Sheets

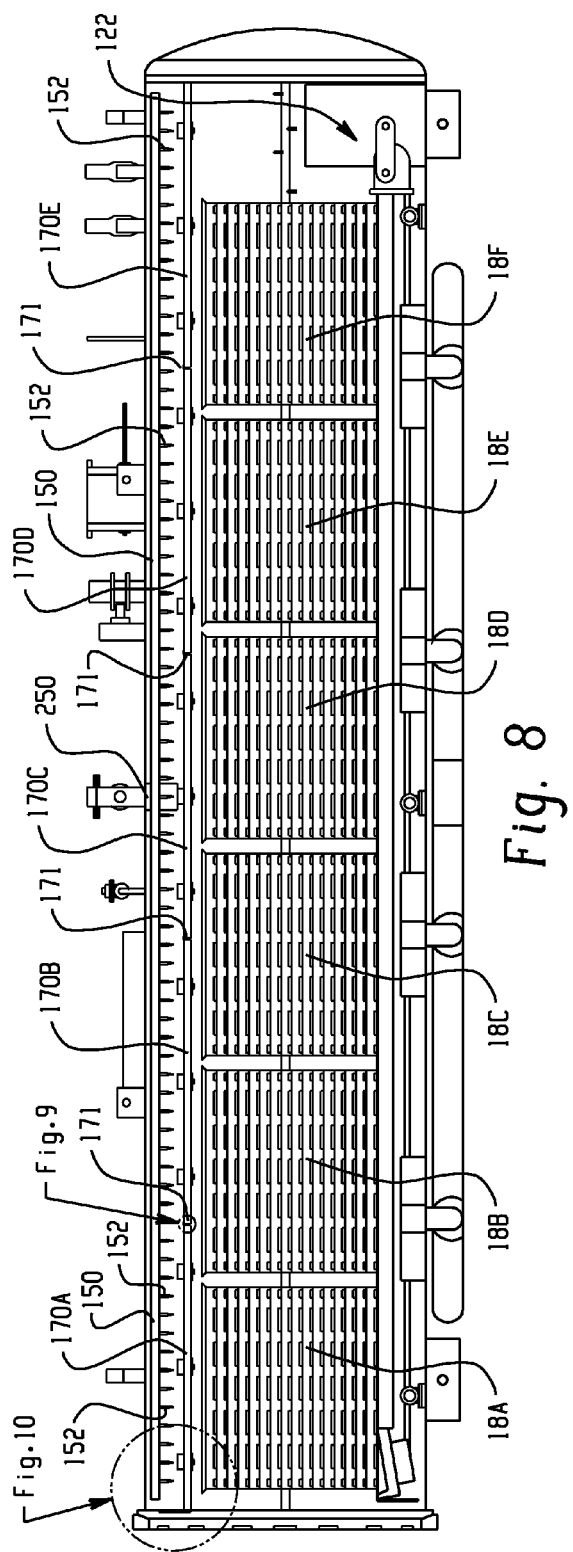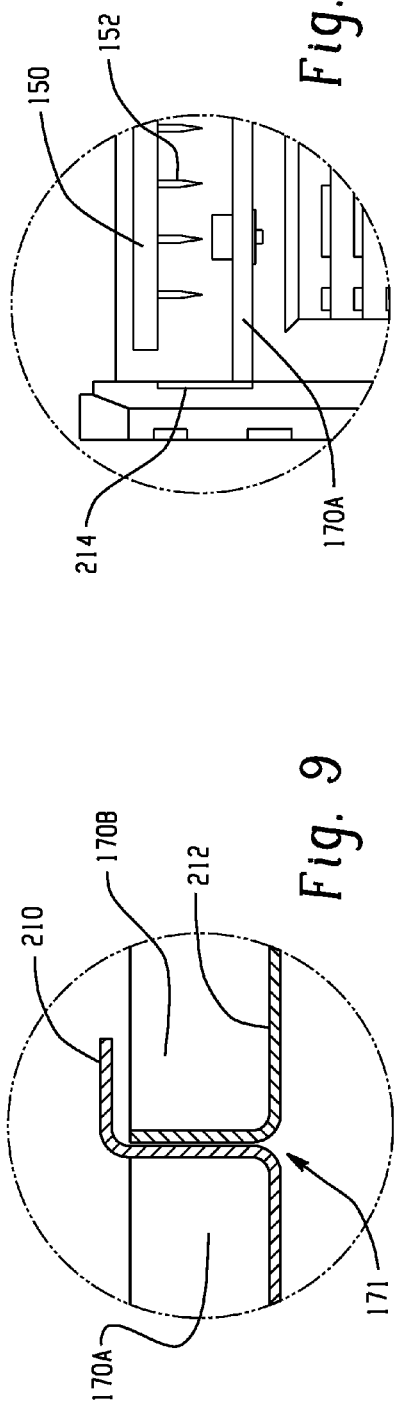
Fig. 8
Fig. 9
Fig. 10

RETORT WITH BAFFLED SPRAY SYSTEM AND RELATED METHODS

CROSS-REFERENCES

This application claims the benefit of U.S. provisional application Ser. No. 61/826,836, filed May 23, 2013, which is incorporated herein by reference.

TECHNICAL FIELD

The present application relates to devices for use in sterilization autoclaves (known in the industry as retorts), and in particular to a system and method for heat treatment of containers of the paperboard type utilizing a combination of sprayed liquid and product movement.

BACKGROUND

To sterilize many foods, pharmaceuticals and other products, to make them "shelf-stable," the products are subjected to a sterilization method by heating the food in its sealed container to a predetermined temperature. The product is held at this temperature for a product specific duration. This process is commonly referred to as an autoclave process, retort process or a sterilization process.

A retort is a pressure vessel commonly used in the food industry for pasteurization and sterilizing low acid food in the container.

Water spray retorting is one of several acceptable commercial processes available in the food industry suitable to run process designed for pasteurizing and sterilizing containers requiring overpressure to ensure integrity of the container. In a water spray process, water is traditionally circulated via a pump circulation loop that draws the water from a sump in the bottom of the retort and pumps the water through a distribution header fitted with spray nozzles at the top and or sides of the retort. The distribution pipes run along the length of the vessel. Steam is used for heating the product in the retort using distribution pipes located in the sump to heat the recirculated water as well as distribution pipes above the sump to distribute saturated steam directly into the load. Compressed air is used to develop overpressure in the retort throughout the process to offset the pressure differential inside the container. Each distribution header has a defined number of spray nozzles that distribute water throughout the product load. There are typically 5-7 headers positioned around the product load. Each nozzle has a given flow and spray angle required to assist with a desired homogeneous heat transfer.

Water cascade retorting is another acceptable commercial processes available in the food industry suitable to run process designed for pasteurizing and sterilizing containers requiring overpressure to ensure integrity of the container. In a water cascade process, water is traditionally circulated via a pump circulation loop that draws the water from a sump in the bottom of the retort and pumps the water through a distribution header oriented at the top and or sides of the retort. The distribution pipes run along the length of the vessel. The header includes openings which allow water to flow down into the into a metal pan that runs the length of the retort above the product. The metal pan typically fills with water to a depth of about 12 mm to 20 mm, and has openings allowing the water to trickle or cascade from the pan (under the head pressure of the water depth in the pan), down to and through the product from the top down through the load. The openings are typically sized and spaced to define such that only between about 3% and about 6% of the pan surface is open. A typical diameter of the openings may be on the order of about 6 mm to 9 mm, with a density distribution to result in a center to center spacing between the openings of about 40 mm. The water is heated in the sump by direct steam or through a heat exchanger in the circulation loop.

For the purpose of treating stationary paperboard containers, U.S. Pat. No. 7,104,465 discloses a water spray retort vessel with at least one processing station and a processing method that includes spraying process fluid onto a container having a paperboard component at a given total flow rate and pressure, where the processing fluid is sprayed onto the paperboard and working at a flow rate and pressure calculated to have a minimal droplet impact on the containers using one or more nozzles producing a solid cone spray pattern at a spray angle in the range of about 100 to about 115 degrees. The '465 patent also discloses that solid cone spray nozzles with higher angles can be used. However, the '465 patent fails to disclose how to calculate droplet impact for almost all spray distances. Moreover, the '465 patent fails to recognize that spraying a container with a minimal droplet impact does not leave room for fluctuations in water pressure during the retort process. Specifically, if the retort is designed to spray at a flow rate and pressure calculated to have a minimal droplet impact on containers while successfully heat treating, then any temporary drop in flow rate or pressure during the process could adversely affect the treatment operation. In other words, by focusing on minimal droplet impact, the '465 patent does not provide an adequately sized processing window for heat treatment of food products.

Modifying the spraying operation to spray with a higher droplet impact can overcome this problem with the '465 patent. However, such a modification can also exacerbate the problem that the '465 patent sought to solve, namely fluid absorption along the exposed edges of paperboard package containers. If there is too much absorption during the treatment process, the package will be considered defective.

Accordingly, what is needed is a system and method that provides an adequate processing window while at the same time avoiding adverse effects on paperboard packaging containers. This goal can be achieved by use of system in which water sprays are disrupted before they ever reach the packaged products being treated.

SUMMARY

In one aspect, a retort includes a vessel having an access door, and a basket supporting assembly within the vessel and supporting multiple product baskets within the vessel. At least one spray pipe is located within the vessel and extends above the product baskets, the spray pipe including a plurality of spray nozzles oriented to spray toward the product baskets. At least one baffle pan is located between the spray nozzles and the product baskets and configured for disrupting water sprays emitted from the spray nozzles before sprayed water reaches the product baskets.

In one implementation of the retort of the preceding paragraph, the baffle pan includes a primary surface portion with a plurality of perforations therein through which sprayed water passes to reach the product baskets or products within the product baskets.

In one example of the retort of either of the two preceding paragraphs, an average vertical spacing between the spray nozzles and the product baskets is between about 110 mm and about 170 mm; and the primary surface portion of the baffle pan is vertically spaced from the product baskets by between about 50 mm and about 70 mm.

In one example of the retort of any of the three preceding paragraphs, a size of the perforations in the baffle pan averages between about 20 mm2 and about 40 mm2.

In one example of the retort of any of the four preceding paragraphs, the perforations are sized and spaced such that between about 10% and about 15% of the primary surface portion of the baffle pan is open.

In one example of the retort of any of the five preceding paragraphs, the retort further includes a system for reciprocating the product baskets back and forth during treatment of products; one or more steam distribution pipes located below the product baskets for emitting steam to flow upward into the product baskets and around the product containers; and a compressed air system for pressurizing the vessel during thermal treatment of the products.

In one example of the retort of any of the six preceding paragraphs, each spray nozzle sprays water at a rate of between about 1.5 gallons-per-minute and about 3.0 gallons-per-minute and has a spray angle of at least 150 degrees.

In one example of the retort of any of the seven preceding paragraphs, the spray nozzles are configured and positioned such that substantially an entirety of the primary surface portion of the baffle pan is covered by water sprays emitted from the spray nozzles.

In one example of the retort of any of the eight preceding paragraphs, at least three spray pipes are located within the vessel and extend above the product baskets, each spray pipe including a plurality of spray nozzles oriented to spray toward the baffle pan.

In one example of the retort of any of the nine preceding paragraphs, no more than three spray pipes with corresponding spray nozzles extend above the product baskets.

In one example of the retort of any of the ten preceding paragraphs, the retort includes a water delivery system for delivering water to the spray nozzles, the water delivery system configured to operate such that each spray nozzles sprays water at a rate that causes no more than about 1.5 mm of water head to build within the baffle pan.

In one example of the retort of any of the preceding paragraph, the water delivery system is configured to operate such that each spray nozzles sprays water at a rate that causes no more than about 1.0 mm of water head to build within the baffle pan.

In one example, the baffle pan is supported within the vessel independent of the product baskets such that the product baskets can be moved in and out of the vessel while the baffle pans remain in place.

In another example, each product basket includes multiple trays loaded therein and arranged in a vertically stacked manner, each baffle pan is formed by an uppermost tray supported atop a respective one of the product baskets, each uppermost tray lacking any product therein such that products in each basket are all below the uppermost tray.

In another aspect, a method is provided for heat treatment of product containers within a retort vessel having multiple spray nozzles for spraying heated liquid toward the product containers. The method involves: reciprocating the product containers back and forth during spraying of the heated liquid; and utilizing at least one perforated baffle member between the spray nozzles and the product containers to disrupt liquid sprays emanating from the spray nozzles before the sprayed liquid reach the product containers by passing through perforations of the baffle member.

In one example of the method of the preceding paragraph, the product containers are located in product baskets that are reciprocated on a rail system within the vessel; the spray nozzles are located above the product baskets; and the baffle member is mounted to the vessel so as to remain stationary as the product baskets and product containers are reciprocated.

In one example of the method of either of the two preceding paragraphs, a size of the perforations in the baffle member averages between about 20 mm2 and about 40 mm2.

In one example of the method of any of the three preceding paragraphs, the perforations are sized and spaced such that between about 10% and about 15% of the baffle member is open.

In one example of the method of any of the four preceding paragraphs, each spray nozzle sprays water at a rate that causes no more than about 1.5 mm of water head to build within the baffle member.

In one example of the method of the three preceding paragraph, each spray nozzle sprays water at a rate that causes no more than about 1.0 mm of water head to build within the baffle member.

In one example of the method of any of the seven preceding paragraphs, the spray nozzles are configured and positioned such that substantially an entirety of the perforate baffle member is covered by water sprays emitted from the spray nozzles.

In one example of the method of any of the eight preceding paragraphs, the method further involves: pressurizing the vessel during the treatment process; and directing steam upward through the product baskets during the treatment process.

In one example of the method, the product containers are located in product baskets that are reciprocated on a rail system within the vessel; the spray nozzles are located above the product baskets; and each product basket includes multiple trays loaded therein and arranged in a vertically spaced apart manner, each baffle pan is formed by an uppermost tray supported atop a respective one of the product baskets, each uppermost tray lacking any product therein such that products in each basket are all below the uppermost tray.

In another aspect, a retort includes a vessel having an access door, and a plurality of spray nozzles located within the vessel for spraying liquid toward product containers within the vessel. At least first and second perforated baffle pans are located between the spray nozzles and the product basket for interacting with liquid sprays emitted from the spray nozzles. The first and second perforated baffle pans are positioned end to end along a depth of the retort, and at least one the first and second baffle pans includes a lip that extends over an abutment joint between the first and second baffle pans to inhibit water sprays from passing directly through the abutment joint.

In one example of the foregoing aspect, the lip is located on the first baffle pan and extends both over the abutment joint and partially above the perforated surface of the second baffle pan.

BRIEF DESCRIPTION OF THE DRAWINGS

FIG. 8 is a side elevation (with vessel internals shown) of the retort of FIG. 5;

FIG. 9 is an enlarged view of a baffle pan abutment joint;

FIG. 10 is an enlarged side view of the front end of the front baffle member;

DETAILED DESCRIPTION

Figure 1:
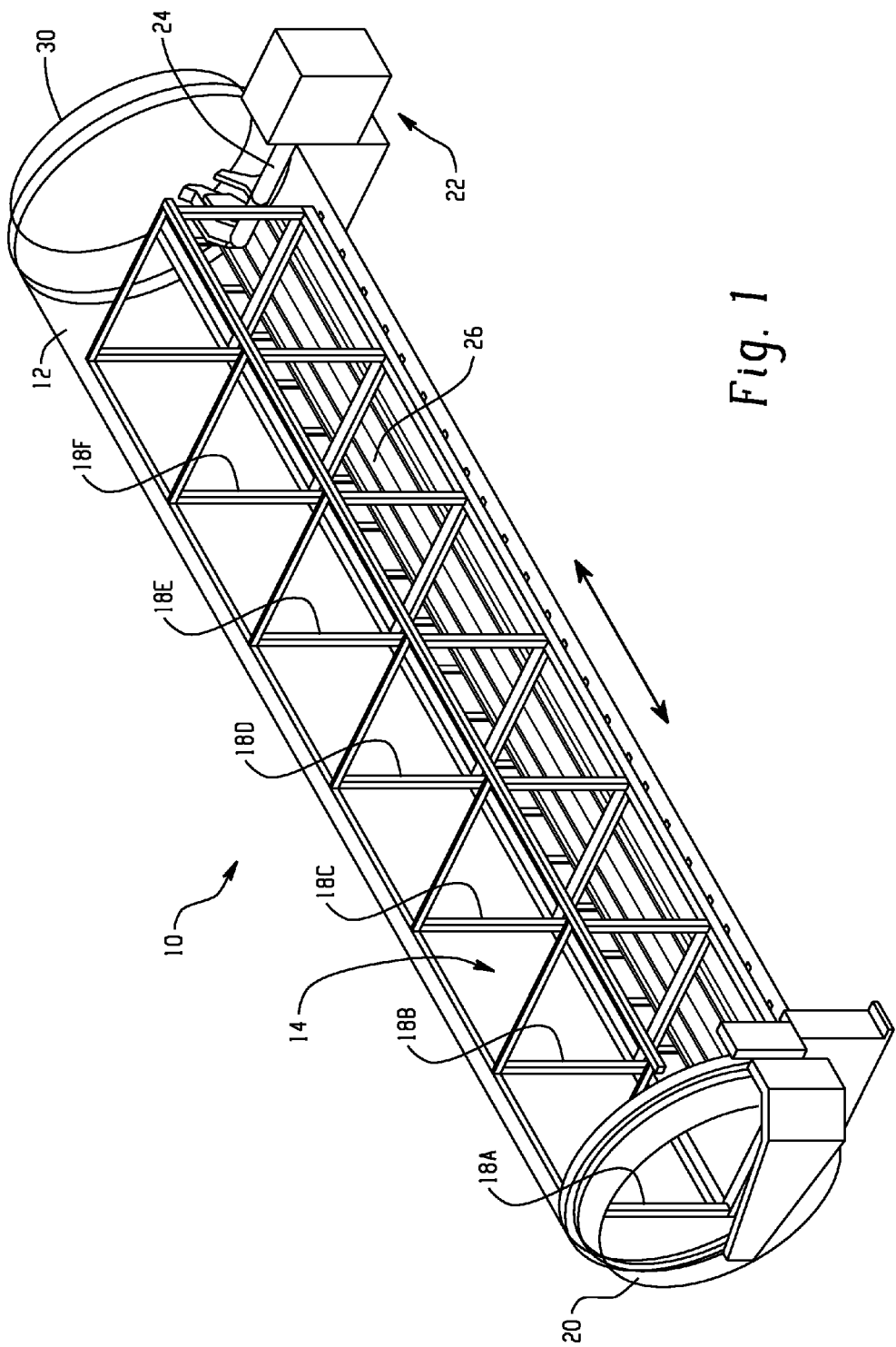
FIG. 1. is a perspective view of a retort vessel.

Referring to FIG. 1, an apparatus 10 (e.g., an autoclave or retort used for cooking and/or sterilization) includes a vessel 12 that defines a basket receiving volume 14 into which a set of baskets 18 are inserted in an end to end arrangement. In FIG. 1 the vessel is shown as transparent, but would typically be of metal construction. By way of example, the inside diameter of the tubular vessel may be in the range of 1000 mm to 2000 mm (e.g., 1400 mm or 1550 mm), but the size of the vessel may vary widely. In the illustrated embodiment each basket 18 is represented by a box-shaped frame structure. Each basket would typically be loaded with multiple product containers (not shown), which may take the form of cans, jars, pouches or any other suitable product package. The containers may include foods, pharmaceuticals or other products that are to be heated within their sealed containers for sterilization and/or cooking.

The vessel 12 includes a hinged door 20 at one end for loading and unloading of the baskets. Generally, the baskets 18 (e.g., six baskets shown here as 18A-18F) including product containers are loaded via an automated shuttle or the like, which urges the baskets into the basket receiving volume 14, then, after processing, retrieves same. Rollers may be provided along a lower part of the basket receiving volume 14, or on the baskets themselves, to support and guide the baskets 18 on their ingress and egress into and out of the vessel, and a frame structure 26, or other basket support assembly, may be located within the vessel for moving the baskets back and forth during the retort process. The frame structure is driven in a reciprocating manner by a motor and drive arrangement 22 that has an associated drive shaft assembly 24 that extends through a wall of the vessel and is operatively couple to the frame. The reciprocating path runs lengthwise from a location toward the door end of the vessel to a location toward the far end 30 of the vessel. In one example, the reciprocation process and structure (including a progressive latch 30 and roller system 40—FIG. 2) may be in accordance with U.S. Patent Publication No. 2013/0039807, which is incorporated herein by reference.

Figure 2:
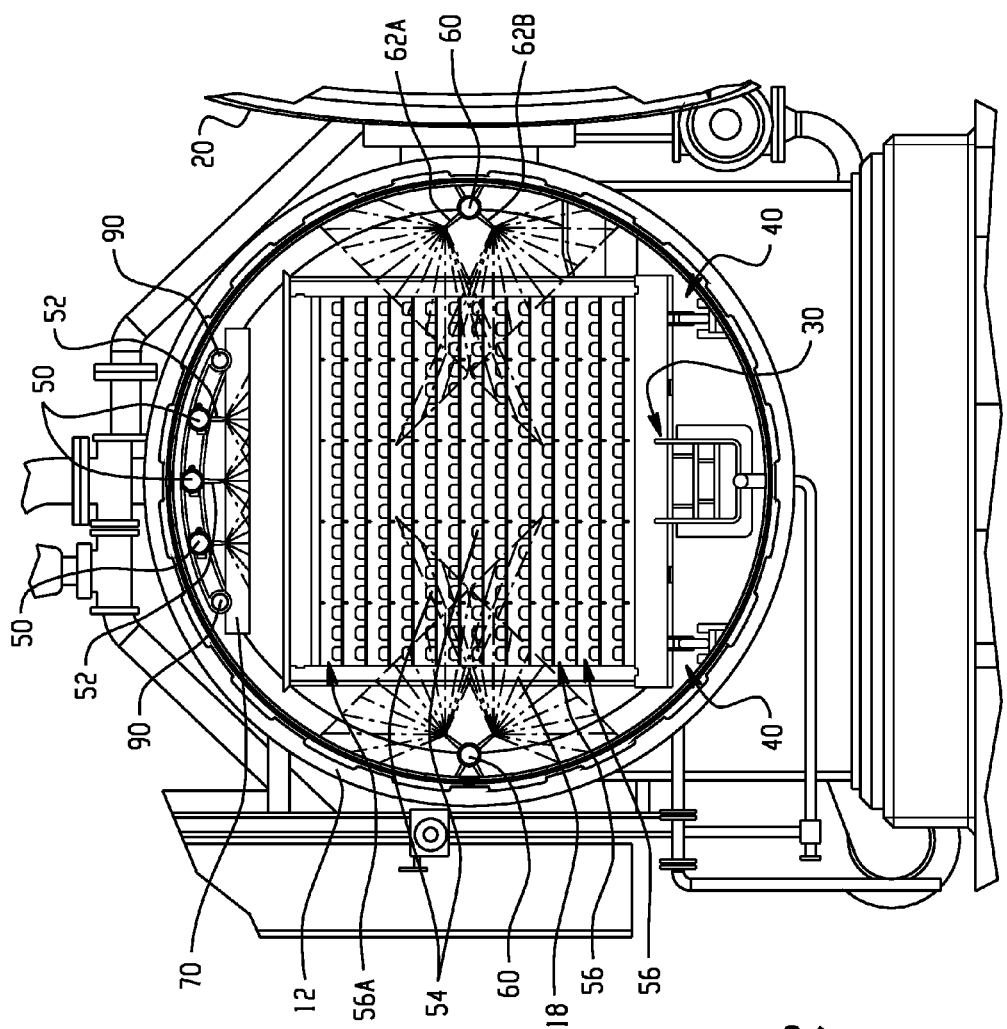
FIG. 2 is an end elevation of a retort vessel with door open.
Figure 3:
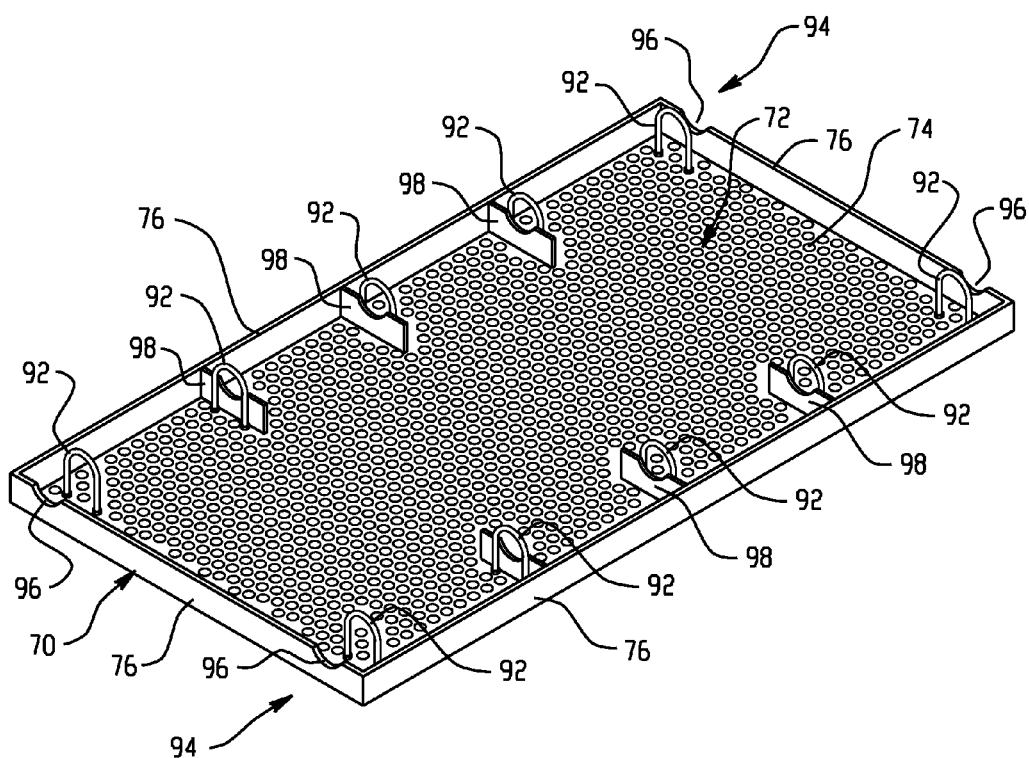
FIG. 3 is a perspective view of a baffle pan configuration.
Figure 4:
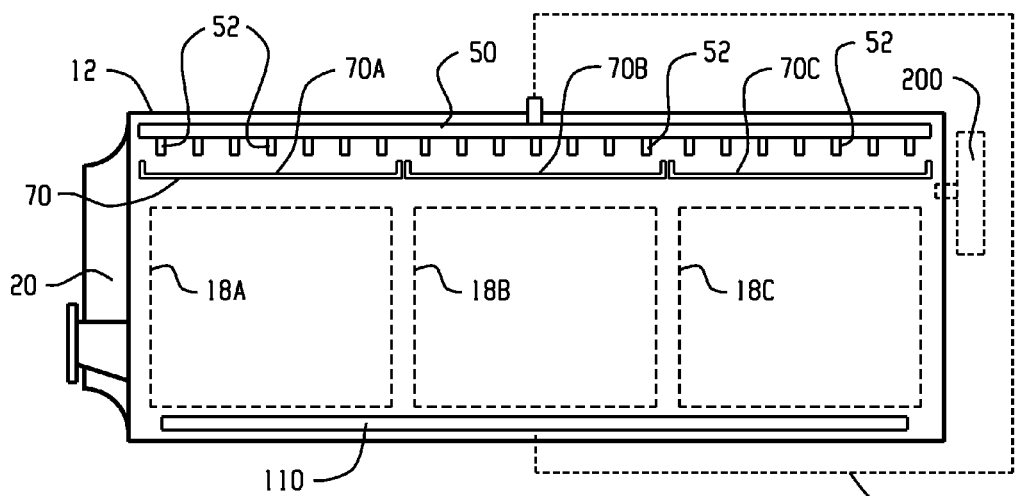
FIG. 4 is a schematic side elevation of a retort vessel.
Figure 6:
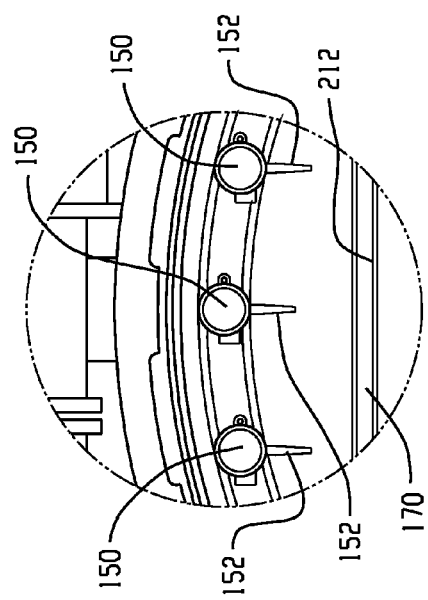
FIG. 6 is an enlarged view of the overhead pipe, nozzle and baffle pan system of FIG. 5.

Referring now to the embodiment shown in FIGS. 2-4, illustrated vessel 12 includes three spaced apart distribution pipes 50 extending lengthwise along the top of the vessel volume (e.g., mounted to the interior surface of the top of the vessel). Each distribution pipe 50 includes a plurality of nozzles 52 spaced apart along the length of the pipe for spraying heated liquid. By way of example, each nozzle may have a spray angle of between about 120 degrees and about 180 degrees (e.g., greater than 150 degrees, such as about 170 degrees), and may be of the solid cone type. For example, a high flow solid cone spray nozzle may be used. However, it is contemplated that other nozzles types may also be used, such as high flow hollow cone spray nozzles. Side located distribution pipes 60 are also provided, with respective nozzles 62 spaced apart along the length of the pipes 60. However, in certain embodiments other spray angles and nozzle types could be used. Notably, the nozzles associated with side-located distribution pipes 60 may have different orientations (e.g., nozzles 62A arranged to spray slightly upward and nozzles 62B arranged to spray slightly downward). Nozzles 62 may also be of a type having a spray angle of between about 120 degrees and about 180 degrees (e.g., greater than 150 degrees, such as about 170 degrees).

As shown in FIG. 2, the baskets 18 include individual product containers 54 loaded thereon, and arranged in vertically spaced apart layers. The top layer 56A of product containers tends to be the most susceptible to damage from the sprays emitted by the nozzles. Accordingly, one or more baffle pans 70 are mounted between the upper nozzles 52 and the product containers, preferably extending the full length or depth of the distribution pipes 50 as suggested in FIG. 4, where only three product baskets 18A-18C are shown schematically for convenience, along with three corresponding baffle pans 70A-70C. A flow path 80 for liquid from the sump of the vessel back up to the top of the vessel is also shown schematically in FIG. 4.

As best seen in FIG. 3, each baffle pan 70 includes a primary surface portion 72 with numerous perforations 74 therein. The perforations may be simple round holes as shown, but other shapes could be used. The primary surface portion 72 is surrounded by upright side and end walls 76 that provide rigidity to the structure. In the illustrated embodiment, the primary surface portion is generally planar. However, it is contemplated that variations in which the primary surface portion is curved (e.g., to mimic the curvature of the vessel) could also be used. As seen in FIG. 2, the sprays emitted by the nozzles of the overhead distribution pipes are directed onto the perforated surfaces of the baffle pans. The baffle pans therefore disrupt or diffuse the sprays in a manner that helps to limit or prevent damage to the product containers 54 in the top layers 56A of the product baskets.

In this regard, it is contemplated that suitable disruption can be obtained where the perforations are sized and spaced such that between about 10% and about 15% of the primary surface portion 72 of the baffle pan is open. Likewise, desirable disruption or diffusion of the sprays has been achieved where a size of the perforations in the baffle plan averages between about 20 mm$^2$ and about 40 mm$^2$ (e.g., between about 25 mm$^2$ and 30 mm$^2$). In the case of circular holes or openings, the diameter may be in the range of about 5 mm to about 7 mm, but it is recognized that non-circular openings could also be used. In one example, a density distribution of the openings to result in a center to center spacing between the openings of less than 20 mm (e.g., about 15 mm) is used. The reduction in product container damage can be best obtained by locating the primary surface portion of the baffle plate as close to the product baskets as possible without interfering with the loading and unloading or the vessel or the reciprocating movement of the containers during treatment. Accordingly, in one example where an average vertical spacing between the spray nozzles 52 and the product baskets 18 is between about 120 mm and about 200 mm, the primary surface portion 74 of the baffle pan(s) is vertically spaced from the product baskets by between about 50 mm and about 70 mm.

The illustrated baffle pans 70 are mounted to spaced apart tubes or rods 90 running lengthwise along the vessel. In particular, each baffle pan includes a plurality of spaced apart U-bolts 92 extending in two spaced apart rows 94. The U-bolts support the baffle pans in a hanging manner from the tubes or rods 90. In this regard, the end walls may include cutouts 96 that also align with the rows 94 to receive the lower portion of the tubes or rods 90 as seen in FIG. 2. In addition, for added stability, the interior of each baffle pan may include one or more upright mount stabilizers 98 (e.g., shaped with a similar recess) to engage with the bottom portion of the tube or rod 90 when the baffle pan is mounted in the vessel. When the U-bolts are tightened, the baffle pans are rigidly secured to the tubes or rods 90. However, the fasteners associated with the U-bolts are accessible from below the baffle pan when the product baskets are removed from the vessel, allowing the baffle pans to be removed for maintenance purposes (e.g., to enable access to the distribution pipes 50 and nozzles 52).

In the illustrated embodiment, there are no baffle pans located between side located spray nozzles 62 and the product baskets. However, variations where baffle pans are also included in this location are possible.

Referring to FIG. 4, one or more steam distribution pipes 110 located below the product baskets are provided for emitting steam to flow upward into the product baskets and around the product containers. A compressed air system 200 for pressurizing the vessel during thermal treatment of the products is also shown schematically.

Turning now to the embodiment of FIGS. 5-11, illustrated vessel 112 includes three spaced apart distribution pipes 150 extending lengthwise along the top of the vessel volume (e.g., mounted to the interior surface of the top of the vessel). Each distribution pipe 150 includes a plurality of nozzles 152 spaced apart along the length of the pipe for spraying heated liquid. By way of example, each nozzle may have a spray angle of between about 120 degrees and about 180 degrees (e.g., greater than 150 degrees, such as about 170 degrees), and may be of the solid cone type. For example, a high flow solid cone spray nozzle may be used. However, it is contemplated that other nozzles types may also be used, such as high flow hollow cone spray nozzles. Side located distribution pipes 160 are also provided, with respective nozzles 162 spaced apart along the length of the pipes 160. As in the previous embodiment, the nozzles 162 associated with side-located distribution pipes 160 may have different orientations. Nozzles 162 may be of the same type as nozzles 152.

Individual product containers 54 are loaded in the baskets 18A-18F, arranged in vertically spaced apart layers. One or more baffle pans 170 are mounted between the upper nozzles 152 and the product containers, preferably extending the full length or depth of the distribution pipes 150 as suggested in FIG. 8. Five baffle pans 170A-170E are utilized, with the pans positioned end to end along the depth of the retort providing four pan abutment joints 171. As seen in FIG. 9, one end of each baffle pan includes a lip feature 210 that extends over the abutment joint 171 between the baffle pans to inhibit water sprays from passing directly through the abutment joint. As shown, the lip 210 is located on the baffle pan 170A and extends both over the abutment joint 171 and partially above the perforated surface 212 of the adjacent baffle pan 170B. Per FIG. 10, the front baffle pan 170A may also include an upward extension 214 to inhibit overspray toward the vessel door 120. The opening size, area and distribution for the openings located in the perforated baffle pan surface 210 is similar to that described above for the embodiment of FIGS. 2-4.

A central header 250 (e.g., fed by a recirculation system with pump, valves and suitable control unit) is used to feed both forward extending and rearward extending pipe sets 150 as seen in FIG. 8. The drive arrangement 122 for reciprocating the product baskets is also shown. Steam and overpressure systems are also provided in the vessel 112.

In operation, each spray nozzle 170 sprays water at a rate that causes no significant build-up of head above the pan surface. Functionally, this results in a different type of water flow onto the product containing baskets than in the cascade type retort. In particular, in the case of the cascade type retort due to the water head above the pan surface the water simply flows from the volume above the surface downward through the openings. In the case of the spray system utilized herein, the lack of head build-up allows the sprays to be diffused by the perforated pan surface (e.g., by interference with the pan surface and edges of the openings, as well as the effect of water film at or across the openings). This desired diffusion can generally be achieved where no more than about 1.5 mm (e.g., no more than about 1 mm) of water head builds within the baffle pan or member (i.e., atop the perforated surface). By properly positioning the spray nozzles, substantially an entirety of the primary or perforated surface portion 212 of the baffle pan is covered by water sprays emitted from the spray nozzles 172. Utilizing large angle spray nozzles (e.g., greater than 150 degrees spray angle) facilitates such coverage.

Figure 7:
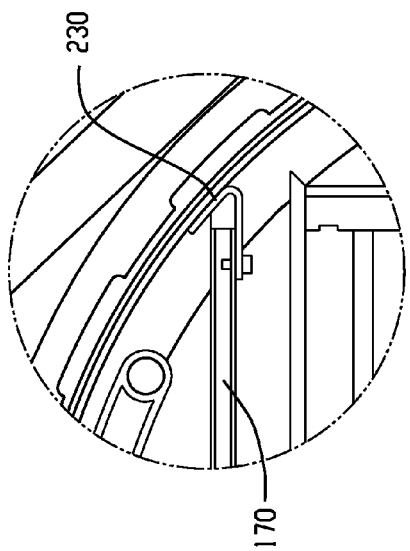
FIG. 7 is an enlarged view of the baffle support system of FIG. 5.
Figure 5:
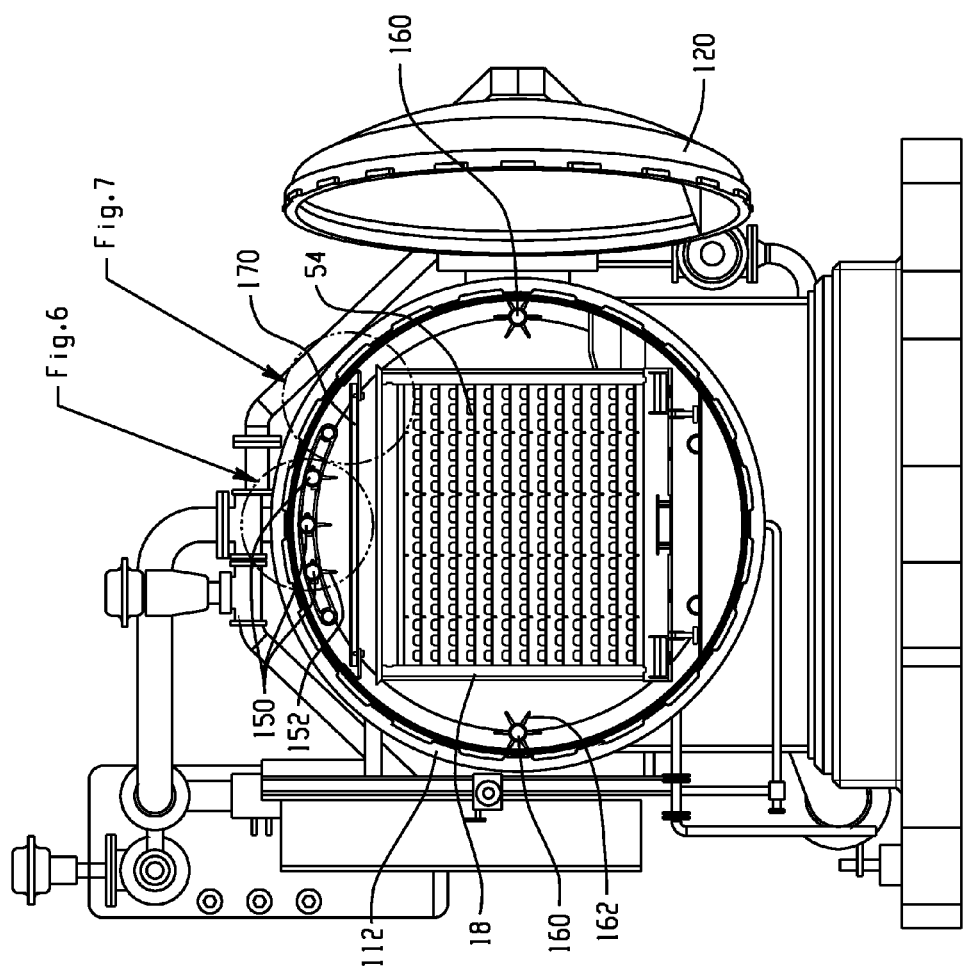
FIG. 5 is an end elevation of another retort embodiment with door open.
Figure 11:
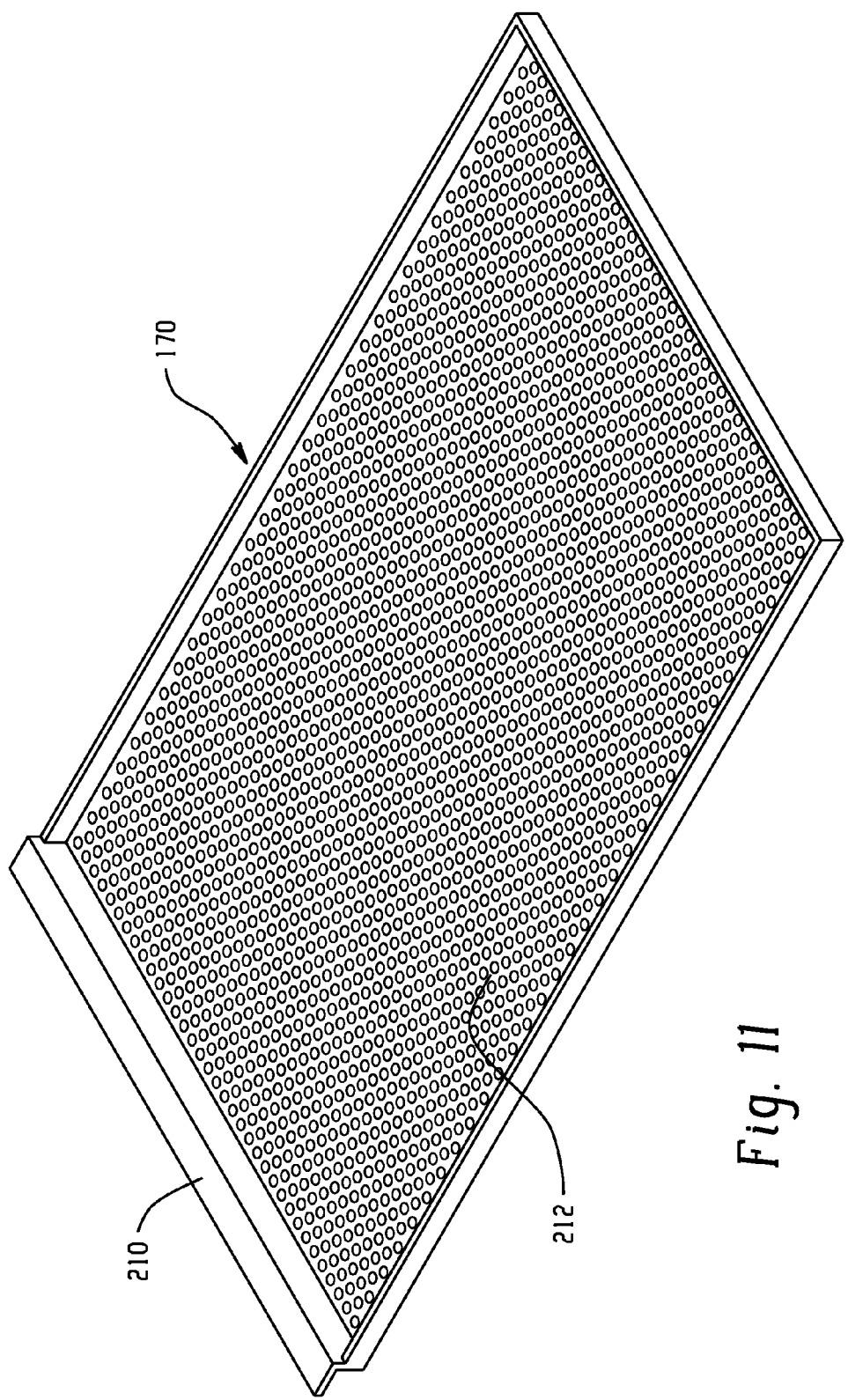
FIG. 11 is a perspective view of an exemplary baffle pan used in the retort of FIG. 5.
Figure 12:
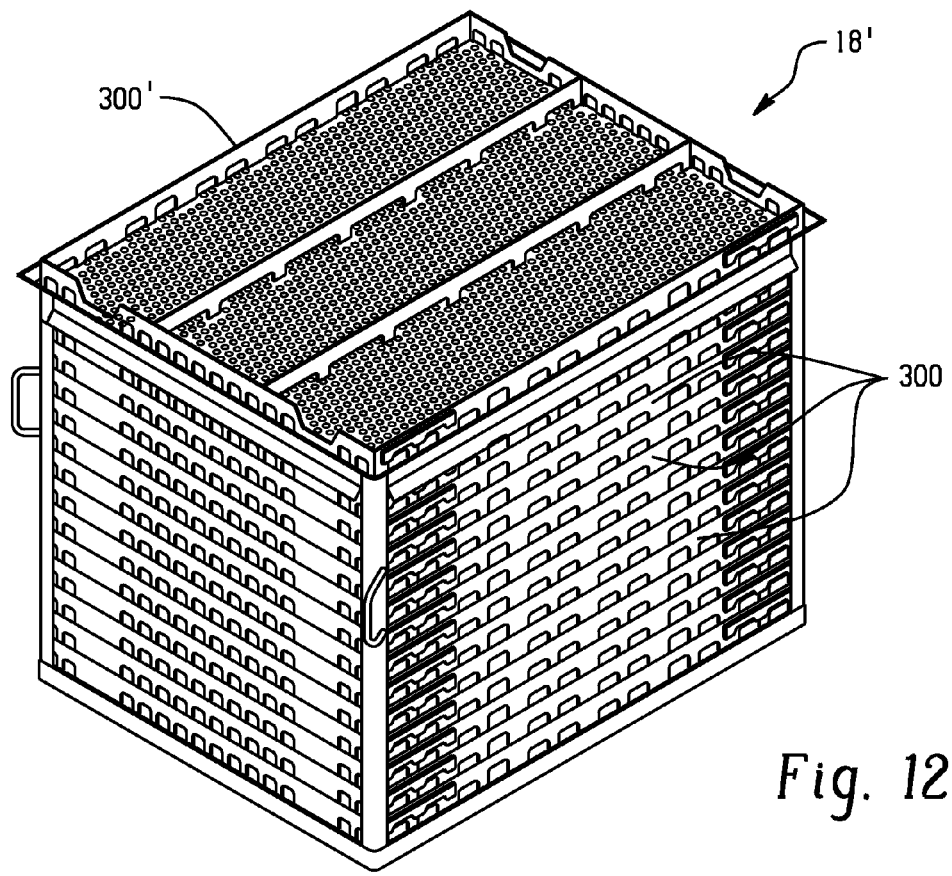
FIG. 12 is a perspective view of a product basket with baffle pan.
Figure 13:
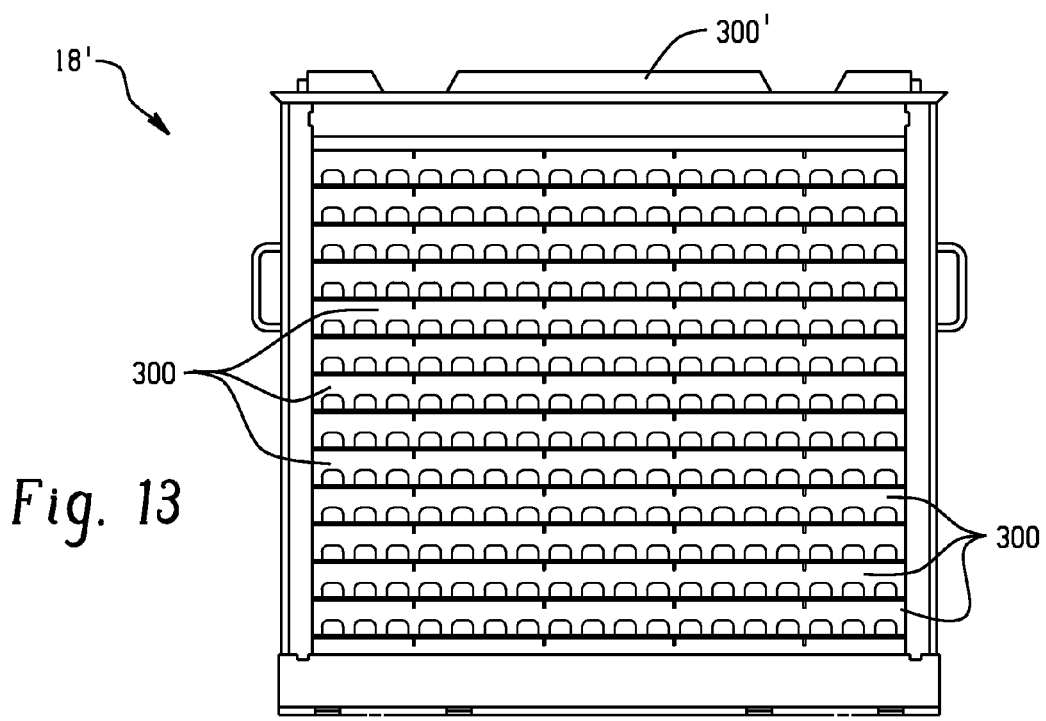
FIG. 13 is a side elevation of the basket of FIG. 12.

Referring to FIG. 7, channel brackets 230 may be provided within the retort enabling the baffle plans to be slid into and out of the vessel. For the purpose of operation, the baffle pans may be bolted to the channel members as shown. Removal of the bolts enables the pans to slide outward.

Figure 14:
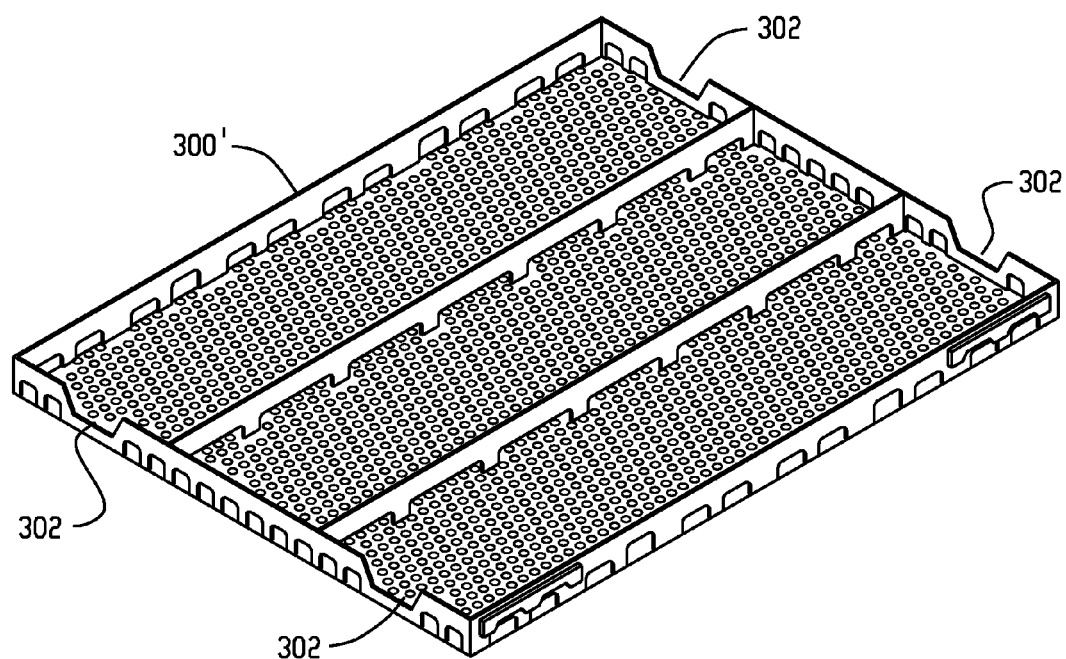
FIG. 14 is a perspective view of the baffle pan used on the basket of FIG. 12.
Figure 15:
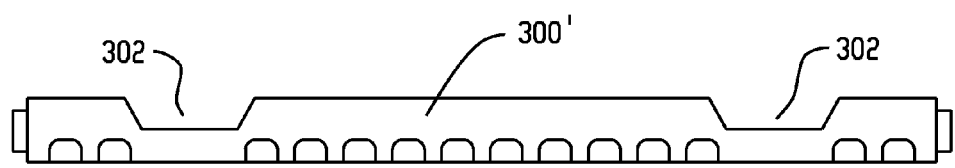
FIG. 15 is a side elevation of the baffle pan of FIG. 14.

Referring now to FIGS. 12-15, an alternative embodiment in which the baffle pan is formed by the uppermost product tray of each product basket is shown. In particular, the exemplary product basket 18' is shown, wilt multiple product trays 300 loaded therein. The trays 300 are arranged in a vertically stacked manner, including an uppermost tray 300'. While the lower trays 300 all support product therein, the uppermost tray 300' is maintained free of product, and the perforated bottom surface of the uppermost tray 300' acts to disrupt the water sprays before they reach the products being treated. The products in each basket are therefore all below the uppermost tray 300' of the basket, assuring that the water sprays do not impact the products directly without first being disrupted by the uppermost tray 300'. As best seen in FIGS. 14 and 15, the upright walls along the of the end portions of the uppermost tray 300' may include reduced height sections 302 that are arranged to align with the location of the lateral water distribution pipes 150 and associated nozzles 152 (see FIG. 6), to assure adequate clearance and avoid any interference with the nozzles that are mounted along the lateral distribution pipes. In this arrangement, the uppermost tray 300' is maintained with each product basket (e.g., the uppermost tray 300' is reciprocated in the same way as the product basket during processing, and moves into and out of the vessel during batch changes).

It is to be clearly understood that the above description is intended by way of illustration and example only and is not intended to be taken by way of limitation, and that changes and modifications are possible.

What is claimed is:

1. A retort, comprising:
   a vessel having an access door;
   a basket supporting assembly within the vessel and supporting multiple product baskets within the vessel;
   at least one spray pipe within the vessel and extending above the product baskets, the spray pipe including a plurality of spray nozzles oriented to spray toward the product baskets;
   at least one baffle pan located between the spray nozzles and the product baskets and configured for disrupting water sprays emitted from the spray nozzles before sprayed water reaches the product baskets;
   wherein the baffle pan is supported within the vessel independent of the product baskets such that the product baskets can be moved in and out of the vessel while the baffle pan remains in place.

2. The retort of claim 1 wherein the baffle pan includes a primary surface portion with a plurality of perforations therein through which sprayed water passes to reach the product baskets or products within the product baskets.

3. The retort of claim 2, wherein:
an average vertical spacing between the spray nozzles and the product baskets is between about 110 mm and about 170 mm; and
the primary surface portion of the baffle pan is vertically spaced from the product baskets by between about 50 mm and about 70 mm.

4. The retort of claim 2 wherein a size of the perforations in the baffle pan averages between about 20 mm$^2$ and about 40 mm$^2$.

5. The retort of claim 2 wherein the perforations are sized and spaced such that between about 10% and about 15% of the primary surface portion of the baffle pan is open.

6. The retort of claim 2, further comprising:
a system for reciprocating the product baskets back and forth during treatment of products;
one or more steam distribution pipes located below the product baskets for emitting steam to flow upward into the product baskets and around the product containers; and
a compressed air system for pressurizing the vessel during thermal treatment of the products.

7. The retort of claim 2, further comprising:
a water delivery system for delivering water to the spray nozzles, the water delivery system configured to operate such that each spray nozzle sprays water at a rate that causes no more than about 1.5 mm of water head to build within the baffle pan.

8. The retort of claim 7 wherein the water delivery system is configured to operate such that each spray nozzles sprays water at a rate that causes no more than about 1.0 mm of water head to build within the baffle pan.

9. The retort of claim 1 wherein each spray nozzle sprays water at a rate of between about 1.5 gallons-per-minute and about 3.0 gallons-per-minute and has a spray angle of at least 150 degrees.

10. The retort of claim 1 wherein the spray nozzles are configured and positioned such that substantially an entirety of the primary surface portion of the baffle pan is covered by water sprays emitted from the spray nozzles.

11. The retort of claim 10 wherein at least three spray pipes are located within the vessel and extend above the product baskets, each spray pipe including a plurality of spray nozzles oriented to spray toward the baffle pan.

12. The retort of claim 11 wherein no more than three spray pipes with corresponding spray nozzles extend above the product baskets.

13. The retort of claim 1 wherein each product basket includes multiple trays loaded therein and arranged in a vertically stacked manner, each baffle pan is formed by an uppermost tray supported atop a respective one of the product baskets, each uppermost tray lacking any product therein such that products in each basket are all below the uppermost tray.

14. A method for heat treatment of product containers within a retort vessel having multiple spray nozzles for spraying heated liquid toward the product containers, the method comprising
reciprocating the product containers back and forth during spraying of the heated liquid; and
utilizing at least one perforated baffle member between the spray nozzles and the product containers to disrupt liquid sprays emanating from the spray nozzles before the sprayed liquid reach the product containers by passing through perforations of the baffle member;
the product containers are located in product baskets movable in and out of the vessel;
the spray nozzles are located above the product baskets;
the baffle member is mounted to the vessel so as to remain stationary as the product baskets are moved in and out of the vessel.

15. The method of claim 14 wherein a size of the perforations in the baffle member averages between about 20 mm$^2$ and about 40 mm$^2$.

16. The method of claim 15 wherein the perforations are sized and spaced such that between about 10% and about 15% of the baffle member is open.

17. The method of claim 15 where each spray nozzle sprays water at a rate that causes no more than about 1.0 mm of water head to build within the baffle member.

18. The method of claim 14 where each spray nozzle sprays water at a rate that causes no more than about 1.5 mm of water head to build within the baffle member.

19. The method of claim 14 wherein the spray nozzles are configured and positioned such that substantially an entirety of the perforate baffle member is covered by water sprays emitted from the spray nozzles.

20. The method of claim 14, further comprising:
pressurizing the vessel during the treatment process; and
directing steam upward through the product baskets during the treatment process.

21. A retort, comprising:
a vessel having an access door;
a plurality of spray nozzles located within the vessel for spraying liquid toward a product basket zone within the vessel;
at least first and second perforated baffle pans located between the spray nozzles and the product basket zone for interacting with liquid sprays emitted from the spray nozzles, wherein the first and second perforated baffle pans are positioned end to end along a depth of the retort, and at least one of the first and second baffle pans includes a lip that extends over an abutment joint between the first and second baffle pans to inhibit water sprays from passing directly through the abutment joint.

22. The retort of claim 21 wherein the lip is located on the first baffle pan and extends both over the abutment joint and partially above the perforated surface of the second baffle pan.

23. The retort of claim 21 wherein the first and second baffle pans are mounted to the vessel so as to remain in position during loading and unloading of the vessel.

24. The retort of claim 23 wherein the first and second baffle pans are removably mounted to the vessel.

* * * * *